United States Patent
Dröge

(10) Patent No.: US 11,952,892 B2
(45) Date of Patent: Apr. 9, 2024

(54) AUTOMATIC GAS SAMPLE HANDLING AND PREPARATION FOR SURFACE DATA LOGGING APPLICATIONS

(71) Applicant: Halliburton Energy Services, Inc., Houston, TX (US)

(72) Inventor: Markus Bernhard Dröge, Sandnes (NO)

(73) Assignee: Halliburton Energy Services, Inc., Houston, TX (US)

( * ) Notice: Subject to any disclaimer, the term of this patent is extended or adjusted under 35 U.S.C. 154(b) by 264 days.

(21) Appl. No.: 17/294,846

(22) PCT Filed: Dec. 19, 2018

(86) PCT No.: PCT/US2018/066463
§ 371 (c)(1),
(2) Date: May 18, 2021

(87) PCT Pub. No.: WO2020/131047
PCT Pub. Date: Jun. 25, 2020

(65) Prior Publication Data
US 2022/0018248 A1    Jan. 20, 2022

(51) Int. Cl.
*E21B 49/08* (2006.01)
*E21B 43/34* (2006.01)
*G01N 1/22* (2006.01)

(52) U.S. Cl.
CPC ............ *E21B 49/081* (2013.01); *E21B 43/34* (2013.01); *G01N 1/2205* (2013.01);
(Continued)

(58) Field of Classification Search
CPC ........ E21B 49/081; E21B 43/34; E21B 49/08; G01N 1/2205; G01N 1/2247; G01N 2001/2267; G01N 2001/227
See application file for complete search history.

(56) References Cited

U.S. PATENT DOCUMENTS

2005/0223829 A1* 10/2005 Mayeaux ............ G01N 17/046
                                                    73/866.5
2009/0193884 A1* 8/2009 Moore ................. E21B 49/008
                                                    73/152.23
(Continued)

FOREIGN PATENT DOCUMENTS

EP          3020916 A1    5/2016

OTHER PUBLICATIONS

International Preliminary Report on Patentability issued in related PCT Application No. PCT/US2018/066463 dated Jul. 1, 2021, 10 pages.
(Continued)

*Primary Examiner* — David Z Huang
(74) *Attorney, Agent, or Firm* — DeLizio, Peacock, Lewin & Guerra, LLP

(57) ABSTRACT

A sample handling system receives a downhole sample. The sample handle system conditions the sample using a separator and filters to allow discharge of unwanted liquids and particulates prior to flowing the sample to one or more analyzers. Separating the moisture and particulates from the sample improves the operation of the components of the sample handling system, for example, by eliminating unwanted condensate or moisture. A coalescing filter, for example, may protect a proportional valve by removing unwanted particulates and liquids from the sample. Additionally, main components of the sample handling system are accessible from a front of a housing to allow for ease of repair and replacement.

20 Claims, 8 Drawing Sheets

(52) U.S. Cl.
CPC ... *G01N 1/2247* (2013.01); *G01N 2001/2267* (2013.01); *G01N 2001/227* (2013.01)

(56) References Cited

U.S. PATENT DOCUMENTS

| | | | |
|---|---|---|---|
| 2014/0298899 A1* | 10/2014 | Schexnaider | G01N 33/2823 165/61 |
| 2016/0032720 A1 | 2/2016 | Schexnaider | |
| 2018/0245466 A1* | 8/2018 | Gosney | E21B 21/067 |

OTHER PUBLICATIONS

International Search Report and Written Opinion issued in related PCT Application No. PCT/US2018/066463 dated Sep. 27, 2019, 13 pages.
"GB Application No. 2106823.4 Examination Report", dated Apr. 25, 2022, 12 pages.

* cited by examiner

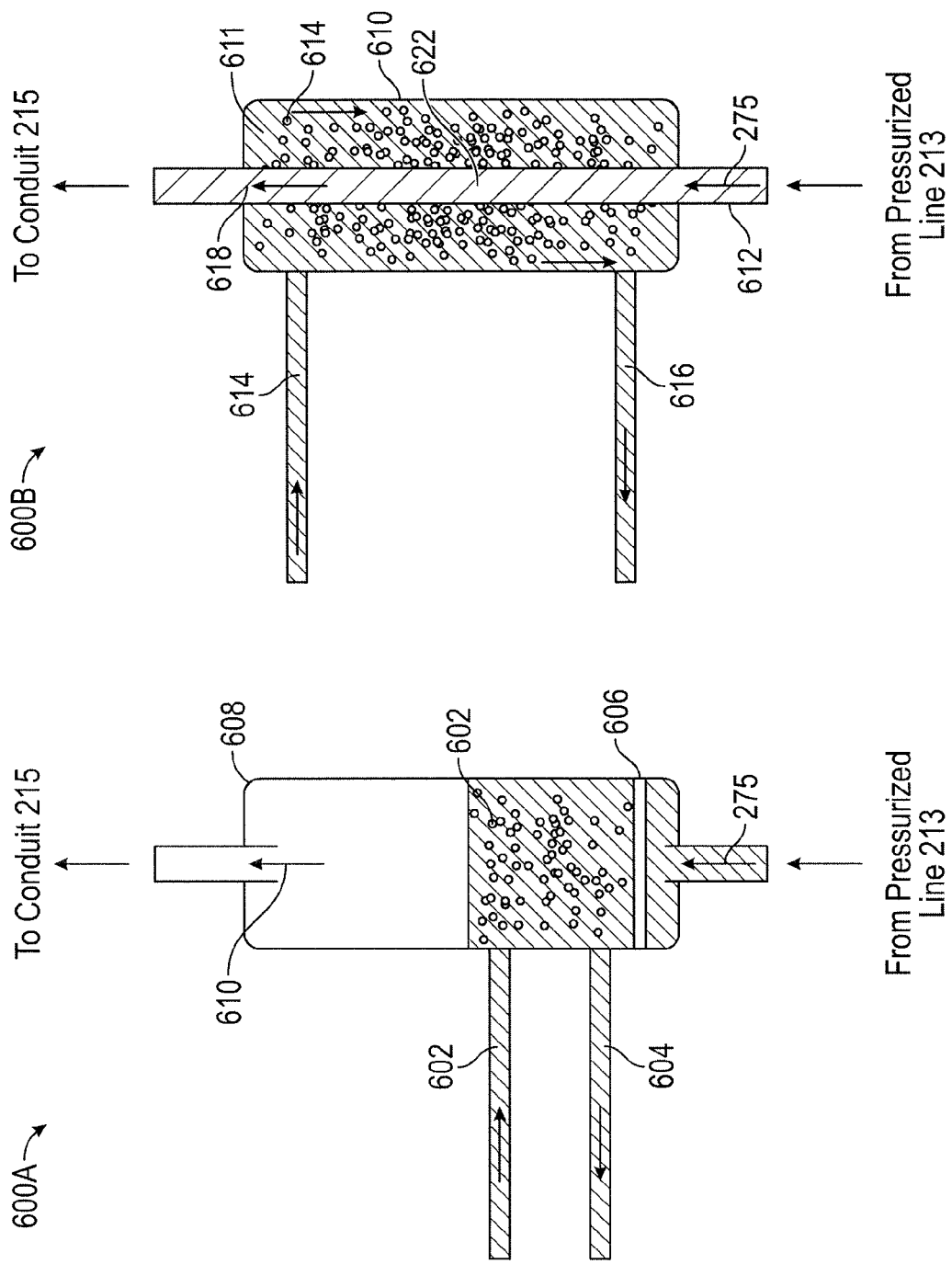

AUTOMATIC GAS SAMPLE HANDLING AND PREPARATION FOR SURFACE DATA LOGGING APPLICATIONS

CROSS-REFERENCE TO RELATED APPLICATION

The present application is a U.S. National Stage Application of International Application No. PCT/US2018/066463 filed Dec. 19, 2018, which is incorporated herein by reference in its entirety for all purposes.

TECHNICAL FIELD

The present disclosure relates generally to downhole drilling operations and, more particularly, to an effective and robust sample data handling apparatus, for example, for surface data logging.

BACKGROUND

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore at a desired well site, treating the wellbore to optimize production of hydrocarbons, and performing the necessary steps to produce and process the hydrocarbons from the subterranean formation.

In certain drilling operations associated with a wellbore, for example, a hydrocarbon drilling operation, condensate coming up in the gas control panel or the remote gas control panel during surface data logging may damage or otherwise affect certain equipment. For example, such condensate may harden equipment towards liquids transported with a sample from the wellbore. Damage to equipment may cause delays in completion of the drilling operation and may increase costs.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features.

FIG. 6A is an example add-on process module, according to one or more aspects of the present disclosure.

FIG. 6B is an example add-on process module, according to one or more aspects of the present disclosure.

Figure 1:
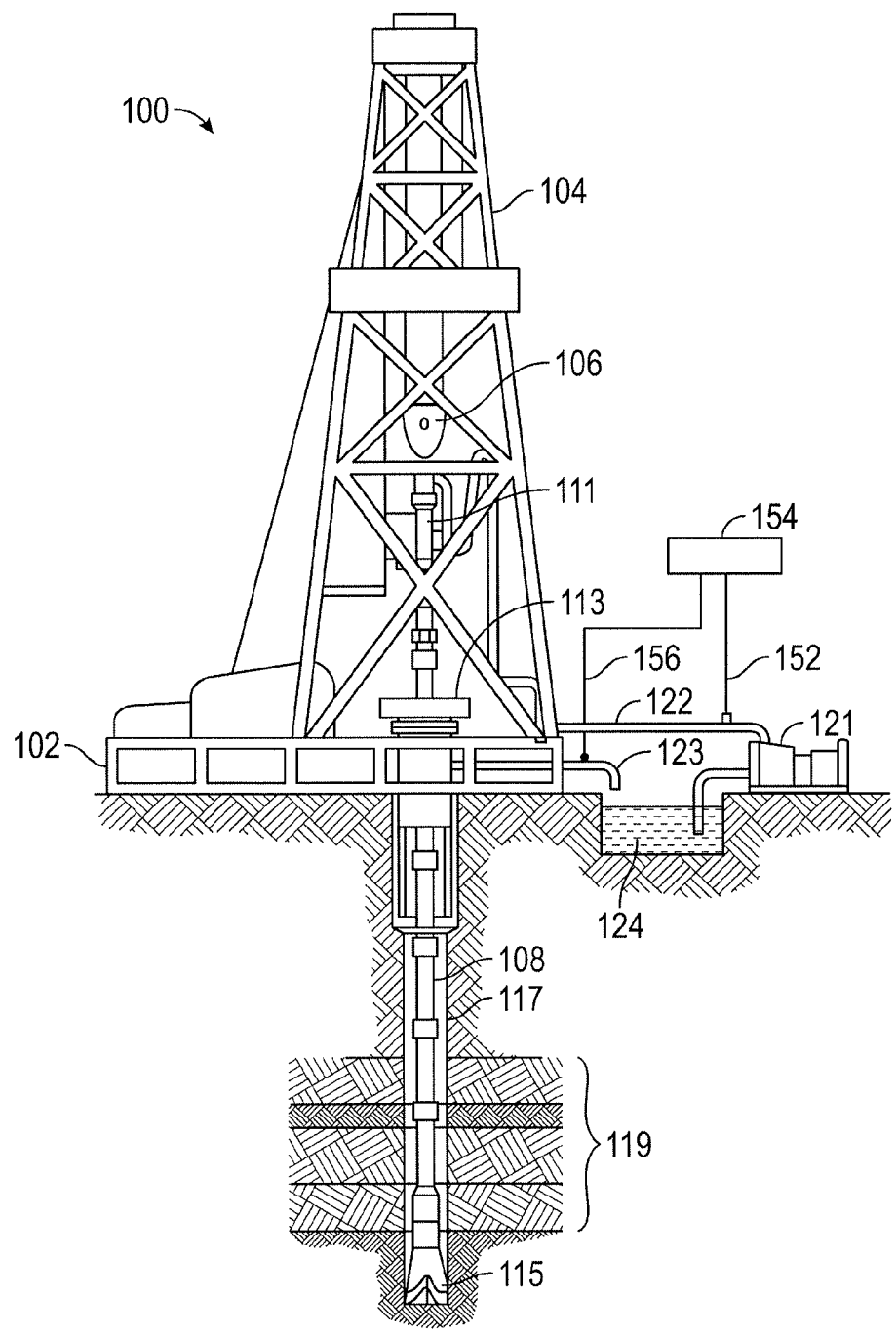
FIG. 1 is a diagram of an example drilling operation environment, according to one or more aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to downhole drilling operations and, more particularly, to a method and systems for producing consistently a sample fluid stream to characterize isotopic composition.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented with tools that, for example, may be conveyed through a flow passage in tubular string or using a wireline, slickline, coiled tubing, downhole robot or the like.

A drilling operation may require various equipment for drilling of a wellbore in a formation, for example, a sample handling system. A sample of one or more fluids, for example, one or more hydrocarbons, liquids, gases, completion fluids, mud or mud filtrates, any other drilling fluids or any combination thereof, may be extracted from the wellbore using a pump, such as a vacuum sample pump. An extracted sample may be used, for example, for surface data logging (SDL). A degasser may be used to remove one or more gasses from the sample. The sample conditioning immediately after extracting the sample from the degasser aims to remove excessive particles and condensate. This removal may be accomplices using one or more coalescent filters and condensation appliances. Condensation that occurs further down the sample line is prevented by the increasing vacuum level towards the sample pump and, in some cases, by a heat traced sample line. Condensation occurs in the sample pump while the sample transits from the deepest vacuum to the highest pressure in the system. For example, the sudden change of pressure causes the liquidus line of the phase diagram to be shifted towards higher temperatures. Further uncontrolled condensation happens during blowback (for example, the pursing of the sample line by injecting compressed air towards the gas trap) in the sample line based also on the above discussed condensation. The majority of condensate from the sample line is caught by an additional coalescent filter, located before the gas control panel (GCP) or the remote gas control panel (rGCP) on the vacuum side of the pump. The resulting liquid is promoted through the entire sample train of GCP or rGCP and may eventually damage filters, pressure regulators or analyzers.

According to one or more aspects of the present disclosure, a sample handling system provides a moisture barrier or trap that prevents damage to the sample handling system. Condensate may accumulate due to several factors for example, due to a pressure change, normal build-up in a filter, incorrect orientation of a component, no or inadequate controlled draining, improper location of a component, and any combination thereof. The present disclosure provides a system and method for hardening the rGCP and extending the GCP towards liquids by protecting the actuators of the sample handling system from excessive moisture and safely discharging upcoming and introduced liquids extracted from the wellbore during a drilling operation and transmitted to the sample handling system. For example, the sample handling system according to one or more aspects of the present disclosure may handle a liquid/sample ratio of approximately 10:1 in extreme situations and severely moisture loaded sample in a completely automated operation. In one or more embodiments, the sample extracted from a borehole or an extracted downhole sample is conditioned using a membrane liquid separator and a coalescent filter are utilized in the membrane liquid separate bypass to protect the backpressure regulator or the proportional valve. According to one or more aspects of the present disclosure, the components of such a sample handling system are less prone to the impact of the above mention factors including faulty design by using a simplified design that automates maintenance tasks.

For example, in one or more embodiments of the present disclosure a pump is capable of being exchanged from the front of the housing of the sample handling system and the membrane of the membrane filter may be exchanged from the front of the housing as well without tools and the necessity to open the enclosure. Additionally, the coalescent filter may be accessible from the exterior of the housing. The draining of the coalescent filter is automatic and does not rely on mechanics or manual intervention to trigger the draining. Thus, the failing condensate management of a standard GCP is remediate according to one or more embodiments of the present disclosure. For example, the sample handling system, according to one or more aspects of the present disclosure, provides autonomous operation, improvement in sample quality, fast and efficient draining of liquids and particles and ease of maintenance.

In one or more aspects of the present disclosure, a well site operation may utilize an information handling system to control one or more operations of conditioning the extracted sample including, but not limited to, retrieval and analysis of information or data associated with a drilling operation, a for example, a sample handling system. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a sequential access storage device (for example, a tape drive), direct access storage device (for example, a hard disk drive or floppy disk drive), compact disk (CD), CD read-only memory (ROM) or CD-ROM, DVD, RAM, ROM, electrically erasable programmable read-only memory (EEPROM), and/or flash memory, biological memory, molecular or deoxyribonucleic acid (DNA) memory as well as communications media such wires, optical fibers, microwaves, radio waves, and other electromagnetic and/or optical carriers and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

FIG. 1 illustrates a drilling operation environment 100 which may be utilized in conjunction with an illustrative embodiment of the present disclosure. A drilling platform 102 is shown equipped with a derrick 104 that supports a hoist 106 for raising and lowering a drill string 108. Hoist 106 suspends a top drive 111 suitable for rotating drill string 108 and lowering it through well head 113. Connected to the lower end of drill string 108 is a drill bit 115. As drill bit 115 rotates, it creates a wellbore or borehole 117 that passes through various formations 119. A drilling fluid circulation system includes a pump 121 for circulating drilling fluid through a supply pipe 122 to top drive 111, down through the interior of drill string 108, through orifices in drill bit 115, back to the surface via the annulus around drill string 108, and into a retention pit 124 via return pipe 123. The drilling fluid transports cuttings from the borehole into pit 124 and aids in maintaining the integrity of wellbore 116. Various materials can be used for drilling fluid, including, but not limited to, a salt-water based conductive mud.

A sample handling system 154 is fluidly coupled to the drilling circulation system via conduit 156 to extract an effluent gas sample from the drilling fluid existing borehole 117 via return pipe 123. Sample handling system 154 is also fluidly coupled to supply pipe 122 via conduit 152 to thereby extract an influent gas sample from drilling fluid entering borehole 117. Sample handling system 154 may be any variety of such devices, as understood in the art.

Figure 2A:
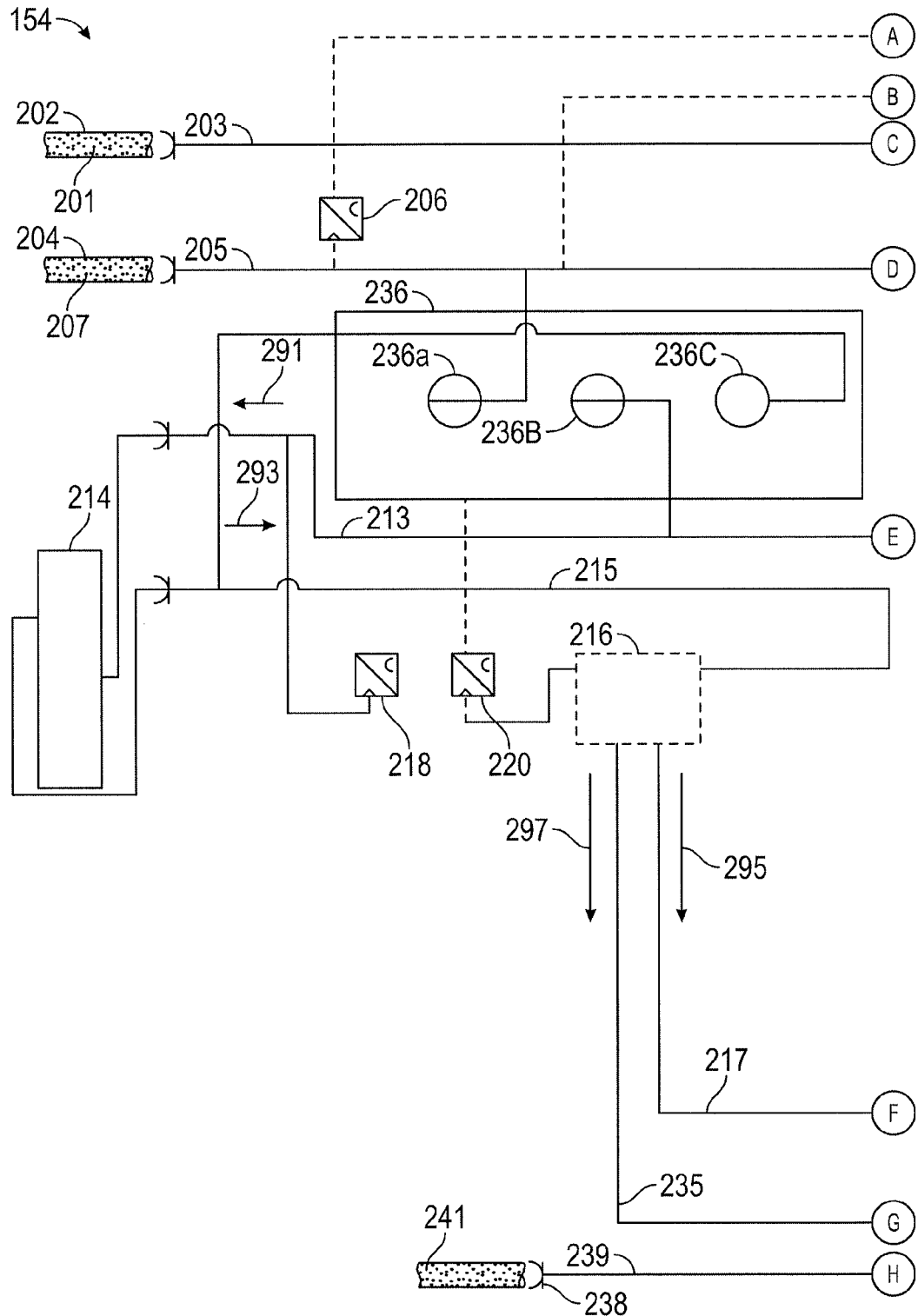
FIG. 2A is a diagram of an example sample handling system, according to one or more aspects of the present disclosure.
Figure 2B:
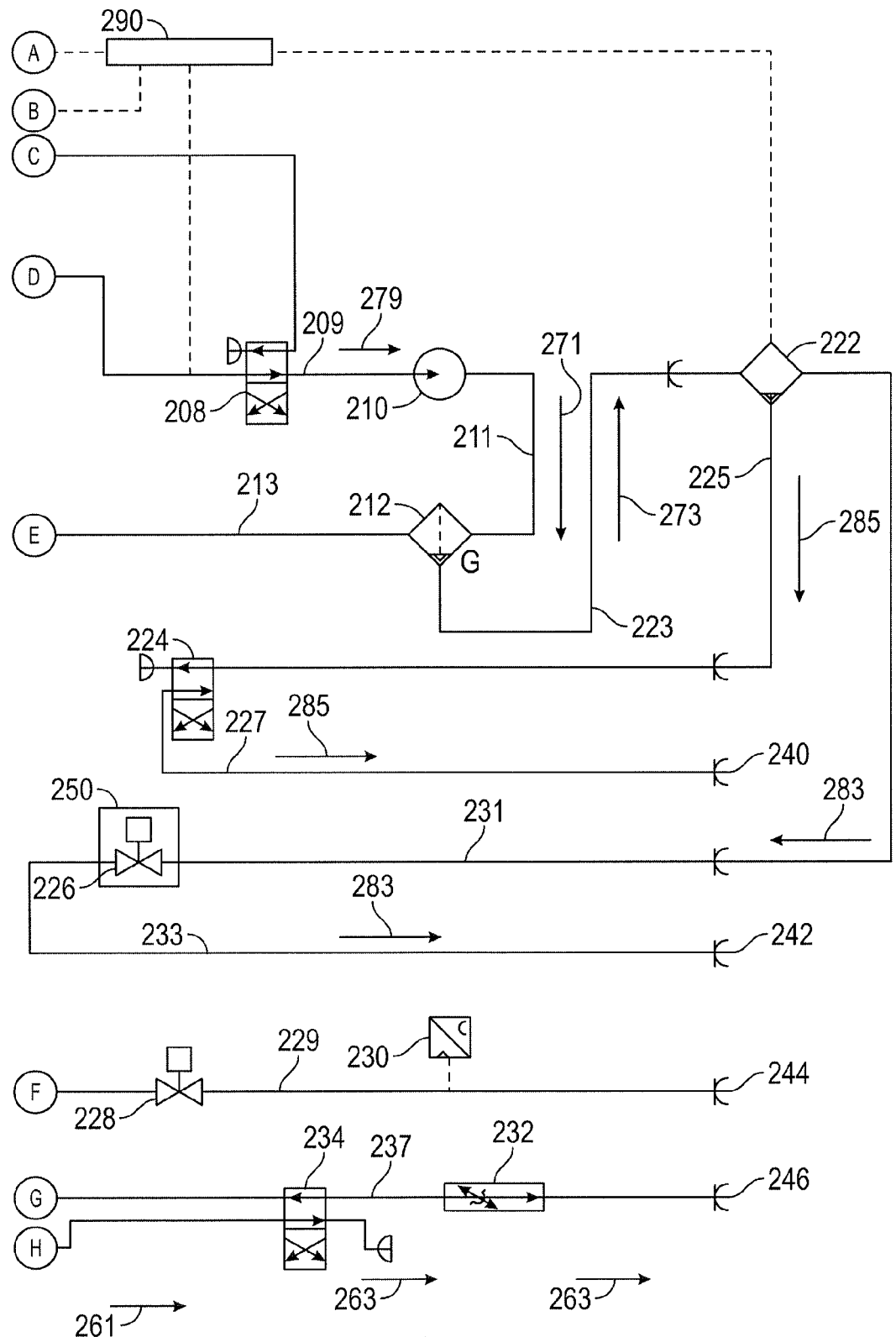
FIG. 2B is a diagram of an example sample handling system, according to one or more aspects of the present disclosure.

FIG. 2A in conjunction with FIG. 2B illustrate an example sample handling system 154 for sampling an extracted fluid from borehole 117. Sample handling system 154 comprises a housing 250. Housing 250 may be at or about nineteen inches in width. The housing 250 allows access to one or more components, for example, pump assembly 210. In one or more embodiments, any one or more elements or components of sample handling system 154 may be coupled wired or wirelessly, directly or indirectly or both to a control system 290. In one or more embodiments, the control system 290 may utilize transmission control protocol (TCP)/Internet (TCP/IP), inter-integrated circuit ($I^2C$) protocol (IP), any other suitable protocol and any combination thereof to communicate with any of the one or more elements or components of sample handling system 154. Control system 290 may comprise one or more information handling systems 700 of FIG. 7.

An extracted fluid 207 from the borehole is received at an input line 205 of the sample handling system 154. Extracted fluid 207 may comprise a gas analyte. In one or more embodiments, input line 205 may be in fluid communication with or is the same as conduit 152 of FIG. 1. In one or more embodiments, the input line 205 includes a suction tube assembly or solenoid 208 for drawing in an extracted fluid 207 and forms a vacuum during a sample intake operation. A transducer 206 may be coupled to input line 205 wired or wirelessly, directly or indirectly, or both. In one or more embodiments, transducer 206 is coupled to the input line 205 proximate to a source 204, for example, at a location between the source 204 and a pump assembly 210. The transducer 206 may be communicatively coupled to control system 290. In one or more embodiments, one or more measurements from the transducer 206 may be used to determine a vacuum, for example, during a sample intake operation, or a pressure, for example, during a blowback operation, in the input line 205. For example, transducer 206 may comprise a pressure transducer and the one or more measurements from the transducer 206 may be communicated to a control system 290 and used to determine a pressure in the input line. The pressure may be compared to a threshold, for example a predetermined pressure threshold. For example, a measurement that is at or above a threshold may be indicative, for example, of a clogged input line 205. In one or more embodiments, a blowback operation may be initiated based, at least in part, on the comparison to unclog the input line 205. In one or more embodiments, a control system 290 based, at least in part, on the one or more measurements, the threshold or both, or a comparison of the aforementioned may trigger a blowback operation. The transducer 206 may also provide one or more measurements to the control system 290 during a blowback operation. The control system 290 may compare the one or more measurements indicative of a blowback pressure to a blowback pressure threshold and may issue, transmit or send a signal or an instruction to continue, discontinue or alter the blowback operation based, at least in part, on the comparison, for example, as discussed with respect to FIG. 4.

In one or more embodiments, one or more additional transducers 236 may couple to input line 205. The one or more additional transducers may comprise transducers 236A, 236B, 236C, collectively additional transducers 236, and any combination thereof. The additional transducers 236 may comprise a moisture transducer, a temperature transducer or both. The additional transducers 236 may be communicatively coupled to the control system 290 wired or wirelessly, directly or indirectly. In any one or more embodiments, one or more types of transducer 236 may be utilized, for example, a temperature transducer, a pressure transducer, a humidity transducer, a dewpoint transducer and any combination thereof.

Input line 205 communicates extracted fluid 207 from a source 204, such as a degasser, to a solenoid 208 disposed or positioned between the pump assembly 210 and the source 204. The solenoid 208 is coupled to a pump assembly 210 via a conduit 209. The extracted fluid 207 is drawn into the input line 205, at least in part, by the pump assembly 210. In one or more embodiments, the pump assembly 210 comprise a peristaltic pump, a vacuum pump, a rotary pump or any other suitable pump. The pump assembly 210 may be disposed such that the pump assembly 210 is directly accessible when inside the housing 250. The solenoid 208 may be a three-way, two position solenoid. During a sampling operation solenoid 208 is in a sample operation state such that solenoid 208 couples the input line 205 to the pump assembly 210 via conduit 209. During a blowback operation, the solenoid 208 is in a blowback state such that the solenoid 208 couples line 203 with input line 205 such that air 201 from an air source 202 is flowed through line 203 to input line 205 and air 202 and any other contaminations or fluid are blocked from the pump assembly 210. In one or more embodiments, air source 202 may comprise any component or module for generating compressed air, for example, compressed air from the drilling environment. For example, solenoid 208 may seal off the pump assembly 210 during a blowback operation to prevent flow of the air 202 to the pump assembly 210. In this way, the input line 205 may be cleaned of any debris without damaging or otherwise affecting any other components of the sample handling system 154. In one or more embodiments, the air 202 is compressed air, for example, from the drilling environment 100.

The pump assembly 210 pumps or draws the fluid 279 through conduit 209. The pumping assembly 210 pressurizes the fluid 279 and pumps the pressurized fluid 271 to a separator 212 via flow line 211. The pump assembly 210 transforms or otherwise converts the vacuum in input line 205 to a pressurized line 213. Condensation of the extracted fluid 207 is minimized due to the increasing vacuum towards the pump assembly 210. One or more components of the fluid 279 may experience a phase change due to the transition from a vacuum to a high pressure resulting in the fluid 279 comprising condensate. In one or more embodiments, separator 212 may comprise a membrane filter. The separator 212 separates at least one of one or more particulates and one or more liquids from the pressurized fluid 271 to form a gas component 291 and a liquids and particulates component 273. The separator 212 is coupled to an add-on process module 214 via the pressurized line 213. The gas component 275 is flowed or communicated from the separator 212 to the add-on process module 214 via the pressurized line 213 while the liquids and particulates component 273 is flowed or communicated to the filter 222. In one or more embodiments, filter 222 may comprise a coalescing filter. In one or more embodiments, an add-on process module 214 is not required and pressurized line 213 is coupled directly to conduit 215.

In one or more embodiments, add-on process module 214 may comprise any one or more modules for further conditioning of the gas component 275. For example, the add-on process module 214 may comprise one or more modules as illustrated in FIGS. 5A-5C, 6A and 6B.

Figure 5A:
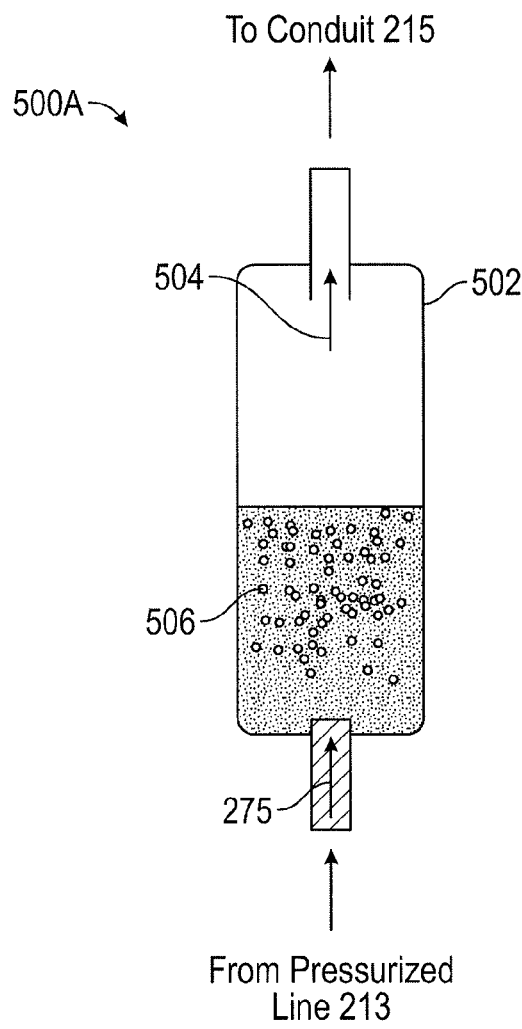
FIG. 5A is an example add-on process module, according to one or more aspects of the present disclosure.

FIG. 5A illustrates an example add-on module that comprises one or more tubes a revolving system 500A. Revolving system 500A comprises one or more tubes 502. A gas component 275 is introduced or flowed into tube 502 via pressurized line 213 where the gas component 275 mixes with one or more powder conditioning agents 506. The one or more powder conditioning agents 506 may comprise sodium sulfate, magnesium sulfate, copper filings, or other agent. The additionally conditioned sample 504 is discharged from the tube 502 to conduit 215.

Figure 5B:
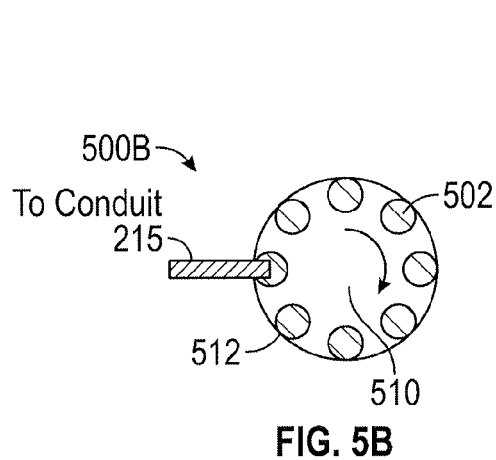
FIG. 5B is an example add-on process module, according to one or more aspects of the present disclosure.
Figure 5C:
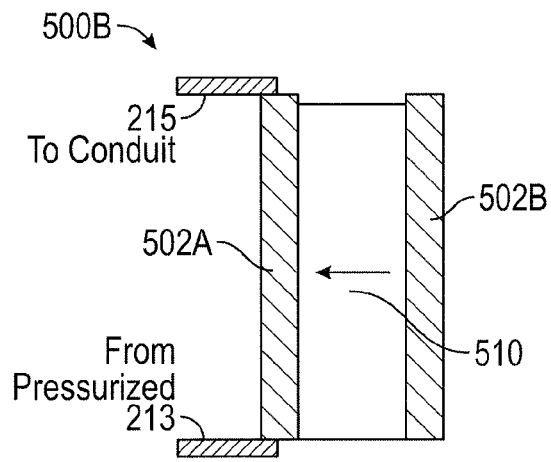
FIG. 5C is an example add-on process module, according to one or more aspects of the present disclosure.

FIG. 5B illustrates a top view of a revolving system 500B that comprises a plurality of tubes 502 in a revolving system 510. Tubes 502 may be disposed with in a holder, aperture or slot 512. Revolving system 510 may rotate to allow an automated exchange of exhausted tubes 502. While a clockwise rotation is indicated in FIG. 5B, the present disclosure contemplates a clockwise or counterclockwise rotation of revolving system 510. FIG. 5C illustrates a side view of a revolving system 500B. As illustrated in FIG. 5C, gas component 275 is flowed to a tube 502A from pressurized line 213 and the additionally conditioned sample 504 is discharged from the tube 502A to conduit 215. Once the contents of tube 502A are discharged, a tube 502B is rotated into position for additional processing of additional gas component 275.

FIG. 6A illustrates an example add-on module that comprises a bubble column reactor 600A, according to one or more aspects of the present disclosure. The bubble column reactor 600A receives gas component 275 from pressurized line 213 at a first end (or bottom) of the bubble column 608. The gas component 275 is mixed with one or more liquid conditioning agents 602, for example, glycol, using sparger 606. Moisture contaminated fluid 604 is discharged from bubble column 608. The additionally conditioned sample 610 is discharged or flowed from the bubble column 608 at a second end (or top) of the bubble column 608 to conduit 215.

FIG. 6B illustrates an example add-on module that comprises a bubble column membrane reactor 600B, according to one or more aspects of the present disclosure. The bubble column membrane reactor 600B comprises an interior membrane tube 622 disposed through exterior tube 610. The inner membrane tube 622 receives gas component 275 from pressurized line 213 at a first end (or bottom) of the interior membrane tube 622. A purge gas 614 is flowed into the exterior tube 610 at or near a top portion of the exterior tube 610 or at a distal end from the first end of the interior membrane tube 622. The interior membrane tube 622 conducts trace moisture, other unwanted substances or both to an interior 611 of the external tube 610. Purge gas 616 is discharged from the external tube 610. The additionally conditioned sample 618 is discharged or flowed from the interior membrane tube 622 to conduit 215.

In one or more embodiments, filter 222 may be exterior to the housing 250. The filter 222 comprises a first output path 225 and a second output path 231. During a blowback operation, solenoid 224 is in an open state and couples path 225 to path 227 which allows a first portion 285 of the liquids and particulates component 273 to be drawn out or discharged through condensate output port 240. In one or more embodiments, the discharge of the first portion 285 is actuated by the filter 222. In one or more embodiments, solenoid 224 may be a three-way, two position solenoid. The solenoid 224 is in a closed state when a blowback operation is not being performed. The second path 231 transmits or flows a second portion 283 that is free or substantially free of any liquids and particulates, for example, the second portion 283 comprises an excess gas that may be trapped in the liquids and particulates components 273. The second portion 283 that is not used for analysis or other processing may be an excess portion (for example, an excess gas portion) of the extracted fluid 207 that is not required for analysis. This second portion 283 may be discharged, drained or exhausted from the filter 222 to exhaust 242. A proportional valve 226 couples the second path 231 to the output path 233 that is coupled to the exhaust 242 when the proportional valve 226 is in an open state, for example, based, at least in part, on a comparison of the pressure in the second path 231 or the filter 222 to a threshold (for example, when pressure in the second path 231 or the filter 222 is at, above or both at or above a threshold). When the proportional valve 226 is in a closed state, for example, based, at least in part, on a comparison of the pressure in the second path 231 or the filter 222 (for example, when pressure in the second path 231 or the filter 222 is at, below or both at or below a threshold), the filter 222 retains the second portion 283. In one or more embodiments, the proportional valve 226 may be in any position between an open state and a closed state such that flow of the second portion 283 is, for example, metered or regulated to the exhaust port 242. Removal of liquids and particulates protects the proportional valve 226 from damage or unnecessary wear and tear.

The gas component 291 from separator 212 is flowed via pressurized line 213 to an add-on process module 214. Add-on process module 214 conditions the gas component 291 to form a sample fluid 293. The sample fluid 293 may be referred to as a dry sample as the liquids and particulates have been extracted by the separator 212. In one or more embodiments, a pressure transducer 218 communicatively couples, wired or wirelessly, directly or indirectly, to pressurized line 213. The pressure transducer 218 monitors the pressure drop over the add-on process module 214. The data from the pressure transducer 218 may be used to predict replacement occurrence for the add-on process module 214, used for quality monitoring so as to provide verification of any one or more measurements.

Sample fluid 293 is flowed via conduit 215 to a sample manifold 216. The sample manifold 216 provides delivery of one or more portions of the sample fluid 293 to one or more analyzers or other equipment of the sample handling system 154. For example, a valve 228 couples a path 217 to path 229 such that a first sample fluid portion 295 of the sample fluid 293 flows to a first analyzer 244. A pressure controller 230 may be coupled to path 229 to regulate pressure of the first sample fluid portion 295 to the first analyzer 244. The first analyzer 244 may comprise a total hydrocarbon analyzer (THA) or total gas analyzer (TGA). One or more measurements from the first analyzer 244 may be indicative of a total hydrocarbon component of the first sample fluid portion 295. In one or more embodiments, one or more operations may be altered, adjusted or terminated based, at least in part, on the one or more measurements from the first analyzer 244. For example, the one or more measurements may be compared to a threshold and an alarm may be triggered, a drilling operation terminated, mud or drilling fluid may be altered or adjusted, any other operation may be performed or any combination thereof based on the comparison.

In one or more embodiments, a transducer 220 is communicatively coupled wired or wireless, directly or indirectly to the sample manifold 216. The transducer 220 monitors pressure of the sample fluid 293 in the sample manifold 216. For example, the transducer 220 generates or provides one or more measurements indicative of pressure of the sample fluid 293 at the sample manifold 216. The transducer 220 may also be communicatively coupled to the control system 290. The one or more measurements from transducer 220 may be compared to a threshold and an operation may be altered or adjusted based, at least in part, on the comparison. For example, if the one or more measurements are indicative of a pressure of the sample fluid 293 or a pressure at the sample manifold 216 at or above a threshold, the proportional valve 226 may be actuated to decrease pressure of the sample fluid 293 received at the manifold 216. In one or more embodiments, the control system 290 may execute one or more instructions that cause the filter 222 or actuation of the proportional valve 226 to drain the second portion 283 (or at least a portion of the second portion 283) so as to decrease pressure of the sample fluid 293 based, at least in part, on the one or more measurements received from the transducer 220, the comparison to the threshold or both. In one or more embodiments, transducer 220 may be communicatively coupled to filter 222 such that filter 222 automatically discharges the second portion 283 based, at least in part, on the one or more measurements from transducer 220.

A second sample fluid portion 297 is flowed from the sample manifold 216 via path 235 to a solenoid 234. Solenoid 234 may be a three-way, two position solenoid. A mass flow controller 232 may be coupled via path 237 to solenoid 234 to control the flow of sample analysis fluid 263 from the solenoid 234 to the second analyzer 246. The second analyzer 246 may comprise a gas chromatograph analyzer or other analysis equipment. In one or more embodiments, one or more measurements from the second analyzer 246 may be indicative of a concentration of one or more different elements of the second sample fluid portion 297, for example, concentration level of one or more different types of gases of the second sample fluid portion 297. In one or more embodiments, at least one of the one or more concentration levels is compared to a threshold and a drilling operation is altered or adjusted based, at least in part, on the comparison.

In one or more embodiments, a calibration gas 241 is supplied via input 238 to path 239. In one or more embodiments, a solenoid 234 is actuated to select between flow of either calibration gas 241 or second sample fluid portion 297 in a direction of 261 to flow controller 232. In one or more embodiments, a solenoid 234 switches flow of the second sample fluid portion 297 from path 235 to one or more analyzers. For example, solenoid 234 may be actuated to switch the flow of the second sample fluid portion 297 from path 235 to path 237 such that sample analysis fluid 263 comprises the second sample fluid portion 297. In another example, solenoid 234 may be actuated to switch the flow of the calibration gas 241 from path 239 to path 237 such that the sample analysis fluid 263 comprises the calibration gas 241. Path 237 couples solenoid 234 to flow controller 232. Flow controller 232 controls the flow of the sample analysis fluid 263 to the second analyzer 246 such that the sample analysis fluid 263 is flow controlled.

Figure 3:
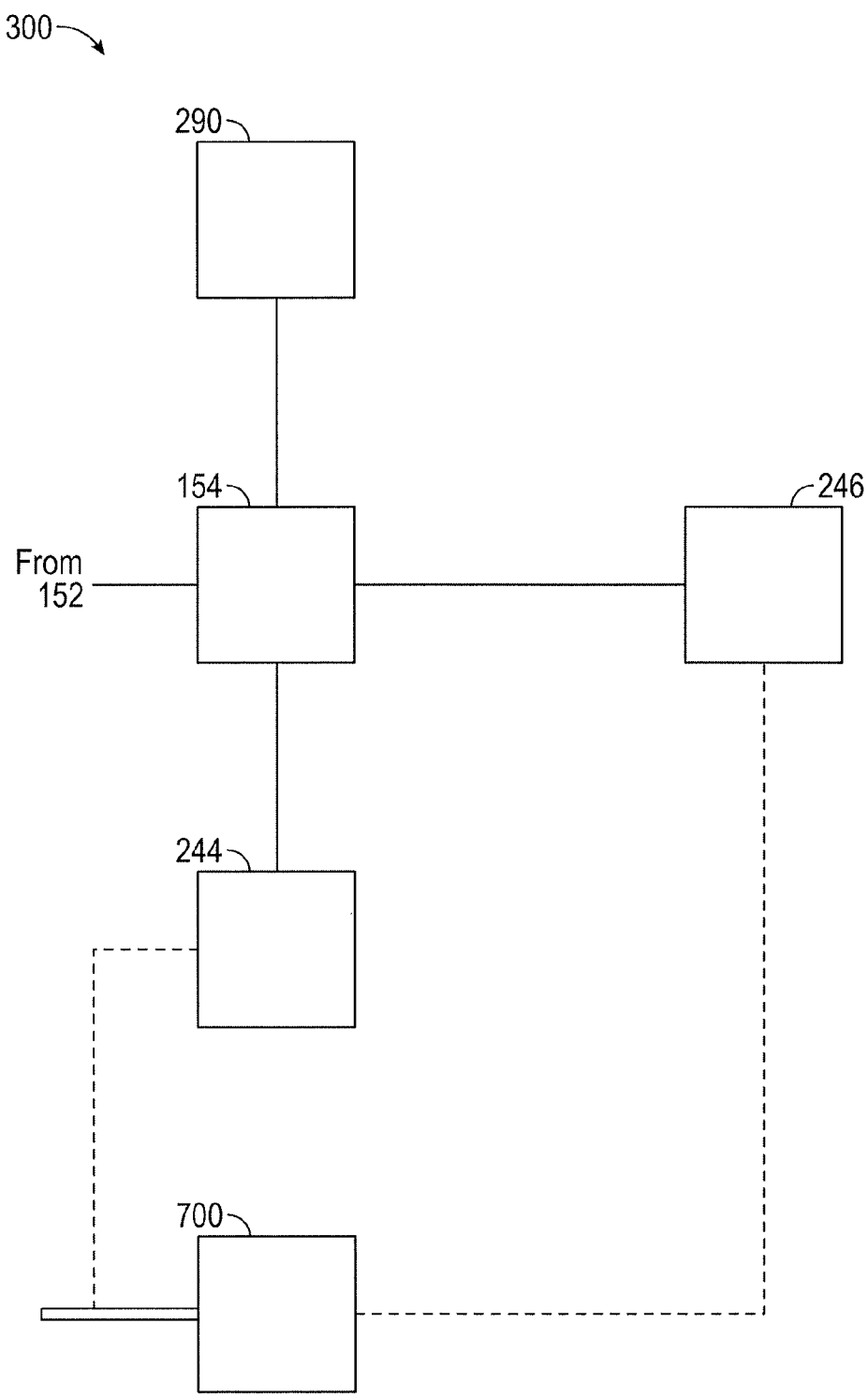
FIG. 3 is a diagram of an example sample analysis system, according to one or more aspects of the present disclosure.

FIG. 3 is a diagram of a sample analysis system 300, according to one or more aspects of the present disclosure. In one or more embodiments, the sample handling system 154 of FIG. 2 receives an extracted fluid 207 from conduit 152. The sample handling system 154 may communicatively couple to control system 290 of FIG. 2, for example, an information handling system 700 of FIG. 7, such that any one or more measurements or information associated with sample handling system 154 may be communicated to the control system 290 for processing. Control system 290 may control one or more operations of one or more components of the sample handling system 154. The sample handling system 154 may communicate or flow sample analysis fluid 263 to a second analyzer 246. The second analyzer 246 analyzes the sample analysis fluid 263 to determine one or more components of the sample analysis fluid 263. One or more measurements, data or information from the second analyzer 246 may be communicated or transmitted to the information handling system 700. The information handling system 700 may store (for example, in a memory or a database), display (for example, plot, graph or otherwise visualize) or otherwise use for additional analysis the one or more measurements, data or information. The information handling system 700 may compare the one or more measurements, data or information to a threshold. Based, at least in part, on the comparison, the information handling system 700 may trigger an alarm, alter, adjust or terminate an operation (for example, stop a drilling operation) or initiate any other procedure or safety measure. For example, a gas threshold may be set such that when a measurement, data or information from the second analyzer 246 reaches, exceeds or both the threshold a signal is sent to terminate drilling, a warning message is communicated, an alarm is triggered or any one or more safety mechanisms are implemented by the information handling system 700. In one or more embodiments, the information handling system 700 may trigger continuous maintenance measures, for example, blowing compressed air 201 to clear out any debris in input line 205. In one or more embodiments, if the first analyzer 244 fades or is taken offline, the second analyzer 246 may provide all necessary analysis to ensure safe operating conditions.

The sample handling system 154 may communicate or flow a first sample fluid portion 295 to a first analyzer 244. In one or more embodiments, first analyzer 244 may comprise a THA, a TGC or any other type of analyzer. The first analyzer 244 analyzes the first sample fluid portion 295 to determine a total hydrocarbon content. The first analyzer may provide one or more measurements, data or information associated with the total hydrocarbon content to an information handling system 700. The information handling system 700 may compare the one or more measurements, data or information to a threshold. The threshold may be a limit set for a particular hydrocarbon content or for a total hydrocarbon content. Based, at least in part, on the comparison, the information handling system may trigger an alarm, alter, adjust or termination an operation (for example, stop a drilling operation) or initiate any other procedure or safety measure. For example, the information handling system 700 may cause the mud composition used in a drilling operation to be altered or adjusted to maintain safe hydrocarbon content levels in the mud.

In one or more embodiments, the analyzer 302, the accumulator 304 or both may be communicatively coupled to an information handling system 700 wired or wirelessly, directly or indirectly. In one or more embodiments, information handling system 700 comprises a plurality of information handling systems 700 such that any one or more of the sample handling system 154, the analyzer 302, the accumulator 304 or any combination thereof couples to one or more information handling systems 700 or one or more different information handling systems 700. In one or more embodiments, the control system 290 and the information handling system 700 are communicatively coupled or are part of the same system.

Figure 4:
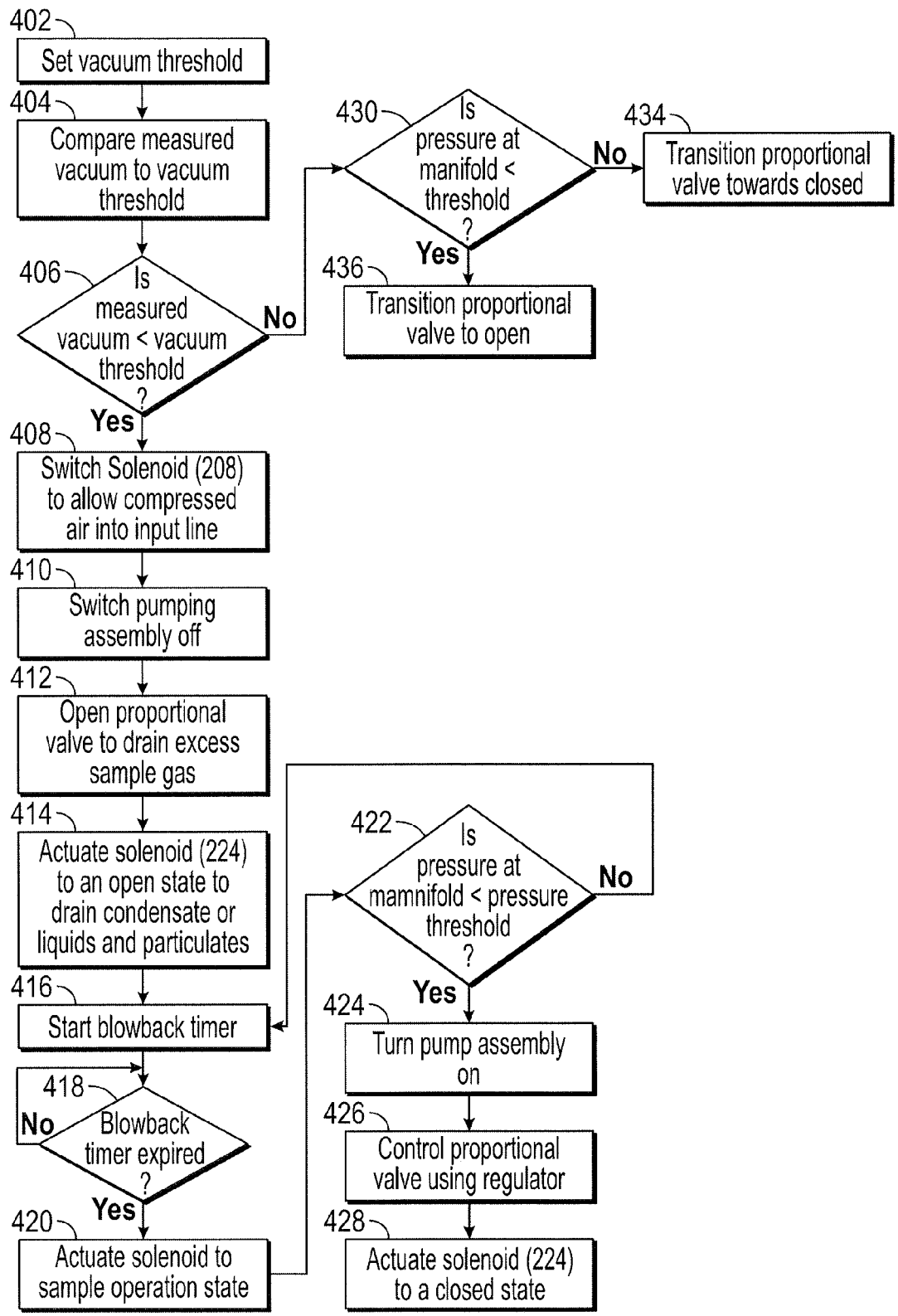
FIG. 4 is a flow chart of an example method for a blowback operation of a sample handling system, according to one or more aspects of the present disclosure.

FIG. 4 is a flow chart of an example blowback operation for a sample handling system 154, according to the present disclosure. As discussed above, during drilling the sample handling system 154 may monitor one or more of the mass, volume or density of the drilling fluid. The results of the measurement may be received, analyzed, and stored by processor 701 of an information handling system 700. One or more sample fluids are extracted from the drilling fluid, as described above. At step 402 a vacuum threshold for the input line 205 is set. At step 404, the measured vacuum from transducer 206 is received at the information handling system 700 and compared to the vacuum threshold.

At step 406, if the measured vacuum is at, below or both the vacuum threshold, the process continues at step 408 where the solenoid 208 is switched or actuated to allow compressed air 202 from line 203 as an input to conduit 209. At step 410, the pump assembly 210 is stopped or switched to an off state so that at step 412, the proportional valve 226 is switched open or actuated to allow excess sample gas from the second portion 283 to drain or exhaust at exhaust 242. At step 414 solenoid 224 is actuated to an open state to drain condensate or liquids and particulates from the first portion 285 to output port 240. In one or more embodiments, step 412 is not required as the pressure due to the excess sample gas from the second portion 283 may be used to assist in draining condensate or liquids and particulates from the first portion 285 to output port 240 and any remaining pressure is also released during the step 412.

At step 416, a blowback timer is initiated. At step 418, expiration of the blowback timer is determined. The process loops at step 418 until the blowback timer expires. At step 420, the solenoid 208 is actuated to a sample operation state such that solenoid 208 couples the input line 205 to the pump assembly 210 via conduit 209. At step 422 the pressure at sample manifold 216 is compared to a pressure threshold. For example, if the pressure at sample manifold 216 remains higher or equal to a pressure threshold the process switches the solenoid 208 as discussed with step 408 and the process continues at step 416. Otherwise the process continues to step 424 where the pump assembly 210 is switched to an on state or turned on. At step 426, the proportional valve 226 is controlled using regulator 250. At step 428, the solenoid 224 is actuated to a closed state.

If at step 406 the comparison indicates that the measured vacuum is greater than or at the vacuum threshold, the process continues at step 430 where the pressure at the sample manifold 216 is determined and compared to a threshold. For example, if the pressure at the sample manifold 216 is less than the threshold then at step 436 the proportional valve 226 is transitioned to an open state (or remains in an open state) and if the pressure at the sample manifold 216 is at or exceeds the threshold then at step 434 the proportional valve is transitioned to a closed state (or remains in a closed state).

Figure 7:
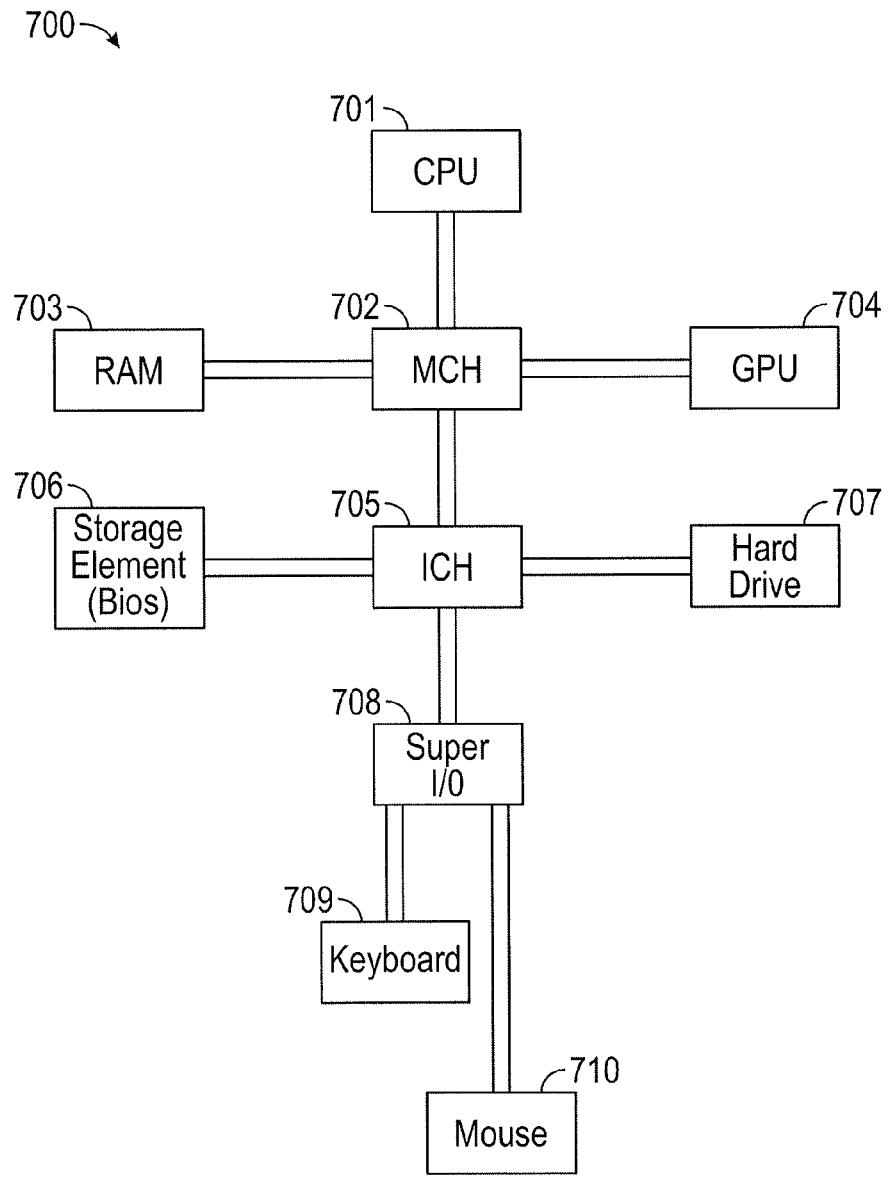
FIG. 7 is a diagram of an example information handling system, according to one or more aspects of the present disclosure.

FIG. 7 is a diagram illustrating an example information handling system 700, according to one or more aspects of the present disclosure. The control system 290 may take a form similar to the information handling system 700. A processor or central processing unit (CPU) 701 of the information handling system 700 is communicatively coupled to a memory controller hub (MCH) or north bridge 702. The processor 701 may include, for example a microprocessor, microcontroller, digital signal processor (DSP), application specific integrated circuit (ASIC), or any other digital or analog circuitry configured to interpret and/or execute program instructions and/or process data. Processor 701 may be configured to interpret and/or execute program instructions or other data retrieved and stored in any memory such as memory 703 or hard drive 707. Program instructions or other data may constitute portions of a software or application for carrying out one or more methods described herein. Memory 703 may include read-only memory (ROM), random access memory (RAM), solid state memory, or disk-based memory. Each memory module may include any system, device or apparatus configured to retain program instructions and/or data for a period of time (for example, computer-readable non-transitory media). For example, instructions from a software or application may be retrieved and stored in memory 403 for execution by processor 701.

Modifications, additions, or omissions may be made to FIG. 7 without departing from the scope of the present disclosure. For example, FIG. 7 shows a particular configuration of components of information handling system 700. However, any suitable configurations of components may be used. For example, components of information handling system 700 may be implemented either as physical or logical components. Furthermore, in some embodiments, functionality associated with components of information handling system 700 may be implemented in special purpose circuits or components. In other embodiments, functionality associated with components of information handling system 700 may be implemented in configurable general purpose circuit or components. For example, components of information handling system 700 may be implemented by configured computer program instructions.

Memory controller hub 702 may include a memory controller for directing information to or from various system memory components within the information handling system 700, such as memory 703, storage element 706, and hard drive 707. The memory controller hub 702 may be coupled to memory 703 and a graphics processing unit (GPU) 704. Memory controller hub 702 may also be coupled to an I/O controller hub (ICH) or south bridge 705. I/O controller hub 705 is coupled to storage elements of the information handling system 700, including a storage element 706, which may comprise a flash ROM that includes a basic input/output system (BIOS) of the computer system. I/O controller hub 705 is also coupled to the hard drive 707 of the information handling system 700. I/O controller hub 705 may also be coupled to a Super I/O chip 708, which is itself coupled to several of the I/O ports of the computer system, including keyboard 709 and mouse 710.

In one or more embodiments, a method for conditioning an extracted downhole sample by a sample handling system, comprising extracting a sample fluid from a borehole, drawing the extracted sample fluid from a source to an input line of the sample handling system using a pump assembly, pressurizing the extracted sample fluid using the pump assembly to transition the extracted sample fluid from a vacuum to a high pressure, separating, by a separator coupled to the pump assembly, from the pressurized extracted sample fluid at least one of one or more particulates and one or more liquids to form a gas component, and wherein a liquids and particulates component is formed by the separated at least one of the one or more particulates and the one or more liquids, flowing the liquids and particulates component to a filter coupled to the separator and discharging from the filter an excess portion of the liquids and particulates components. In one or more embodiments, the method further comprises determining a pressure at the input line based on one or more measurements from a pressure transducer coupled to the input line proximate to the source, comparing the pressure to a pressure threshold and initiating a blowback operation based, at least in part, on the comparison. In one or more embodiments, the method further comprises switching a solenoid to a blowback state, wherein the solenoid is coupled to the input line between the pump assembly and the source and flowing an air through the input line, wherein the solenoid seals off the pump assembly to prevent flow of the air to the pump assembly. In one or more embodiments, the method further comprises flowing a first portion of the gas component to a first analyzer, measuring a total hydrocarbon component of the first portion by the first analyzer and altering a drilling operation based, at least in part, on a comparison of the total hydrocarbon component to a threshold. In one or more embodiments, the method further comprises flowing a second portion of the gas component to a second analyzer, measuring one or more concentration levels of one or more elements of the gas component by the second analyzer and altering a drilling operation based, at least in part, on a comparison of at least one of the one or more concentration levels to a threshold. In one or more embodiments, the method further comprises flowing the gas component to an add-on process module coupled to the separator. In one or more embodiments, the method further comprises controlling, by a flow controller, flow of the gas component to the second analyzer.

In one or more embodiments, a sample handling system comprises an input line coupled to a source, a pump assembly coupled to the input line, wherein the pump assembly draws an extracted fluid from a source through the input line, a high pressure line coupled to the pump assembly, wherein the pump assembly pressurizes the extracted fluid through the high pressure line, a separator coupled to the high pressure line, wherein the separates from the pressurized extracted sample fluid at least one of one or more particulates and one or more liquids to form a gas component, and wherein the liquids and particulates component is formed by the separated at least one of the one or more particulates and the one or more liquids, a filter coupled to the separator, wherein the filter receives an excess portion of the liquids and particulates component and an output port coupled to the filter, wherein the filter discharges the excess portion to the output port. In one or more embodiments, the system further comprises a transducer coupled to the input line proximate to the source, wherein the pressure transducer generates a measurement indicative of a pressure at the input line. In one or more embodiments, the system further comprises a solenoid coupled to the input line between the pump assembly and the source, wherein the solenoid switches to a blowback state based, at least in part, on the measurement, and wherein the solenoid seals off the pump assembly to prevent flow of air to the pump assembly during the blowback state. In one or more embodiments, the system further comprises a first output path of the filter, a second output path of the filter, wherein the first output path couples to a condensate output port and wherein the second output path couples to an exhaust. In one or more embodiments, the system further comprises a solenoid coupled to the first output path, wherein the solenoid allows a portion of the liquids and particulates component to be discharged through the condensate output port. In one or more embodiments, the system further comprises a proportional valve coupled to the second output path, wherein the proportional valve allows an excess gas portion of the liquids and particulates component to be discharged to the exhaust. In one or more embodiments, the sample handling system further comprises a manifold coupled to the separator and one or more analyzers, wherein the one or more analyzers receive the gas component from the manifold. In one or more embodiments, the one or more analyzers comprise at least a total hydrocarbon analyzer or a gas chromatograph analyzer. In one or more embodiments, the system further comprises a transducer coupled to the manifold, wherein the transducer measures pressure at the manifold. In one or more embodiments, the system further comprises one or more add-on process modules coupled to the separator, wherein the one or more add-on process modules further condition the gas component.

In one or more embodiments, a sample analysis system comprises a control system, a sample handling system communicatively coupled to the control system, wherein the sample handling system comprises an input line coupled to a source, a pump assembly coupled to the input line, wherein the pump assembly draws an extracted fluid from a source through the input line, a high pressure line coupled to the pump assembly, wherein the pump assembly pressurizes the extracted fluid through the high pressure line, a separator coupled to the high pressure line, wherein the separates from the pressurized extracted sample fluid at least one of one or more particulates and one or more liquids to form a gas component, and wherein the liquids and particulates component is formed by the separated at least one of the one or more particulates and the one or more liquids, a filter coupled to the separator, wherein the filter receives an excess portion of the liquids and particulates component and an output port coupled to the filter, wherein the filter discharges the excess portion to the output port. In one or more embodiments, the system further comprises a transducer coupled to the input line proximate to the source, wherein the pressure transducer generates one or more measurements indicative of a pressure at the input line and wherein the control system receives the one or more measurements from the transducer, and wherein the control system triggers a blowback operation based, at least in part, on the one or more measurements. In one or more embodiments, the system further comprises a first output path of the filter, a second output path of the filter, wherein the first output path couples to a condensate output port and wherein the second output path couples to an exhaust and a proportional valve coupled to the second output path, wherein the control system actuates the proportional valve to discharge an excess gas portion of the liquids and particulates component to the exhaust.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee. The indefinite articles "a" or "an," as used in the claims, are each defined herein to mean one or more than one of the element that it introduces.

What is claimed is:

1. A method for conditioning an extracted downhole sample by a sample handling system, comprising:
 extracting a sample fluid from a borehole;
 drawing the extracted sample fluid from a source to an input line of the sample handling system using a pump assembly;
 increasing the pressure of the extracted sample fluid using the pump assembly to transition the extracted sample fluid from a vacuum to a pressure higher than the vacuum;
 separating, by a membrane separator coupled in-line with the pump assembly, from the extracted sample fluid having an increased pressure at least one of one or more particulates and one or more liquids to form a gas component, and wherein a liquids and particulates component is formed by the separated at least one of the one or more particulates and the one or more liquids;

flowing the liquids and particulates component to a filter coupled to the membrane separator; and discharging from the filter an excess portion of the liquids and particulates component.

2. The method of claim 1, further comprising:

determining a pressure at the input line based on one or more measurements from a pressure transducer coupled to the input line proximate to the source;

comparing the pressure to a pressure threshold; and initiating a blowback operation based, at least in part, on the comparison.

3. The method of claim 2, further comprising:

switching a solenoid to a blowback state, wherein the solenoid is coupled to the input line between the pump assembly and the source; and flowing an air through the input line, wherein the solenoid seals off the pump assembly to prevent flow of the air to the pump assembly.

4. The method of claim 1, further comprising:

flowing a first portion of the gas component to a first analyzer;

measuring a total hydrocarbon component of the first portion by the first analyzer; and altering a drilling operation based, at least in part, on a comparison of the total hydrocarbon component to a threshold.

5. The method of claim 1, further comprising:

flowing a second portion of the gas component to a second analyzer; and measuring one or more concentration levels of one or more elements of the gas component by the second analyzer; and altering a drilling operation based, at least in part, on a comparison of at least one of the one or more concentration levels to a threshold.

6. The method of claim 1, further comprising flowing the gas component to an add-on process module coupled to the membrane separator.

7. The method of claim 5, further comprising controlling, by a flow controller, flow of the gas component to the second analyzer.

8. A sample handling system, comprising:

an input line coupled to a source;

a pump assembly coupled to the input line, wherein the pump assembly draws an extracted fluid from a source through the input line;

a high pressure line coupled to the pump assembly, wherein the pump assembly increases the pressure of the extracted fluid through the high pressure line to a pressure higher than a vacuum;

a membrane separator coupled in-line with the high pressure line, wherein the membrane separator separates from the extracted fluid having an increased pressure at least one of one or more particulates and one or more liquids to form a gas component, and wherein a liquids and particulates component is formed by the separated at least one of the one or more particulates and the one or more liquids;

a filter coupled to the membrane separator, wherein the filter receives an excess portion of the liquids and particulates component; and an output port coupled to the filter, wherein the filter discharges the excess portion to the output port.

9. The sample handling system of claim 8, further comprising:

a transducer coupled to the input line proximate to the source, wherein the pressure transducer generates a measurement indicative of a pressure at the input line.

10. The sample handling system of claim 9, further comprising a solenoid coupled to the input line between the pump assembly and the source, wherein the solenoid switches to a blowback state based, at least in part, on the measurement, and wherein the solenoid seals off the pump assembly to prevent flow of air to the pump assembly during the blowback state.

11. The sample handling system of claim 8, further comprising:

a first output path of the filter; and a second output path of the filter;

wherein the first output path couples to a condensate output port; and wherein the second output path couples to an exhaust.

12. The sample handling system of claim 11, further comprising a solenoid coupled to the first output path, wherein the solenoid allows a portion of the liquids and particulates component to be discharged through the condensate output port.

13. The sample handling system of claim 11, further comprising a proportional valve coupled to the second output path, wherein the proportional valve allows an excess gas portion of the liquids and particulates component to be discharged to the exhaust.

14. The sample handling system of claim 8, further comprising:

a manifold coupled to the membrane separator; and one or more analyzers, wherein the one or more analyzers receive the gas component from the manifold.

15. The sample handling system of claim 14, wherein the one or more analyzers comprise at least a total hydrocarbon analyzer or a gas chromatograph analyzer.

16. The sample handling system of claim 14, further comprising a transducer coupled to the manifold, wherein the transducer measures pressure at the manifold.

17. The sample handling system of claim 8, further comprising one or more add-on process modules coupled to the membrane separator, wherein the one or more add-on process modules further condition the gas component.

18. A sample analysis system, comprising:

a control system;

a sample handling system communicatively coupled to the control system, wherein the sample handling system comprises:

an input line coupled to a source;

a pump assembly coupled to the input line, wherein the pump assembly draws an extracted fluid from a source through the input line;

a high pressure line coupled to the pump assembly, wherein the pump assembly increases the pressure of the extracted fluid through the high pressure line to a pressure higher than a vacuum;

a membrane separator coupled in-line with the high pressure line, wherein the membrane separator separates from the extracted fluid having an increased pressure at least one of one or more particulates and one or more liquids to form a gas component, and wherein the liquids and particulates component is formed by the separated at least one of the one or more particulates and the one or more liquids;

a filter coupled to the membrane separator, wherein the filter receives an excess portion of the liquids and particulates component; and an output port coupled to the filter, wherein the filter discharges the excess portion to the output port.

19. The system of claim 18, further comprising:

a transducer coupled to the input line proximate to the source, wherein the pressure transducer generates one or more measurements indicative of a pressure at the input line; and wherein the control system receives the one or more measurements from the transducer, and wherein the control system triggers a blowback operation based, at least in part, on the one or more measurements.

20. The system of claim 18, further comprising:

a first output path of the filter;

a second output path of the filter, wherein the first output path couples to a condensate output port, and wherein the second output path couples to an exhaust; and a proportional valve coupled to the second output path, wherein the control system actuates the proportional valve to discharge an excess gas portion of the liquids and particulates component to the exhaust.

\* \* \* \* \*